(12) United States Patent
Gottlöber

(10) Patent No.: US 6,248,963 B1
(45) Date of Patent: Jun. 19, 2001

(54) BALE-DENSITY MEASURING SYSTEM FOR BALER

(75) Inventor: Dietrich Gottlöber, Neustadt (DE)

(73) Assignee: Case Harvesting Systems GmbH, Neustadt (DE)

( * ) Notice: Subject to any disclaimer, the term of this patent is extended or adjusted under 35 U.S.C. 154(b) by 0 days.

(21) Appl. No.: 09/368,103

(22) Filed: Aug. 3, 1999

(30) Foreign Application Priority Data

Aug. 4, 1998 (DE) .............................. 198 35 166

(51) Int. Cl.$^7$ .................................................. G01G 19/08
(52) U.S. Cl. .............................. 177/136; 177/145; 702/50
(58) Field of Search ................................... 177/136, 137, 177/138, 139, 141, 145; 702/50

(56) References Cited

U.S. PATENT DOCUMENTS

| 2,982,201 | 5/1961 | Kruger | 177/161 |
|---|---|---|---|
| 3,427,870 | 2/1969 | Merriman | 177/136 |
| 4,742,880 | * 5/1988 | Schrag et al. | 177/136 |
| 5,384,436 | * 1/1995 | Pritchard | 177/136 |
| 5,742,010 | 4/1998 | Griffin | 177/136 |
| 5,811,739 | * 9/1998 | Palmore | 177/136 |
| 5,990,422 | * 11/1999 | Komori et al. | 177/25.11 |

FOREIGN PATENT DOCUMENTS

| 27 34 766 | 2/1978 | (DE) . |
|---|---|---|
| 38 20 367 | 12/1989 | (DE) . |
| 36 89 937 | 7/1990 | (DE) . |
| 295 11 023 U | 11/1995 | (DE) . |
| 44 36 128 | 3/1996 | (DE) . |
| 196 40 061 | 4/1998 | (DE) . |
| 0 233 350 | 9/1985 | (EP) . |
| 0 233 351 | 5/1987 | (EP) . |
| 577428 | 10/1977 | (SU) . |

\* cited by examiner

*Primary Examiner*—Randy W. Gibson
(74) *Attorney, Agent, or Firm*—Herbert Dubno; Andrew Wilford

(57) ABSTRACT

Bales are produced by a baler having a pressing passage of predetermined cross section and from which emerges a succession of the bales that travel rearward from the press passage over an output guide and fall off a rear edge of the guide from the baler. The density of these bales is determined by weighing each of the bales in the guide and producing a weight output corresponding to a weight of the bale in the guide and measuring the length of each of the bales in the guide and producing a length output corresponding to a length of the bale in the guide. Then the volume of each of the bales is calculated by multiplying the respective bale length output by an area equal to the cross section of the passage and each calculated volume is divided by the respective weight output to derive the density of the respective bale.

8 Claims, 5 Drawing Sheets

BALE-DENSITY MEASURING SYSTEM FOR BALER

FIELD OF THE INVENTION

The present invention relates to a baler. More particularly this invention concerns a system for measuring the density of bales produced by a baler.

BACKGROUND OF THE INVENTION

Straw is particularly useful as animal bedding, horticultural mulch, and for industrial and commercial purposes such as in insulation and packing materials. Straw is produced by cutting standing crop and, normally after stripping off any useful part, spreading it on the field to dry for some time. Hay is the more useful part of the standing crop that is similarly cut and dried in the field, but that is subsequently used as animal fodder or ensilage.

In order to turn the loose straw or hay into a product that can be transported, stored, and accounted for, it is pressed into bales. For commercial purposes the so-called large-format square bale, which is actually parallepipedal, is used. It is produced in a baler that picks the cut crop up off the ground, normally comminutes it somewhat, presses it into bales, applies ties around the bales, and drops the bales on the field behind the machine. In view of the pace of the baling operation, it is normally more expedient for the baler simply to leave a trail of bales in the field that are later picked up by a different crew operating at a different pace.

Ideally, all of the bales produced should be of the same size and weight. The size is determined by the bale length, width, and height. The width and height are established by the size of the pressing passage and the length by the cycling time of the tying device of the baler. The weight is clearly a function of size, and also of the density of the bale, that is how tightly or loosely the straw or hay is packed in it.

The press passage typically has side walls that can be moved horizontally by hydraulic actuators to narrow or widen the width of this passage. Since the downstream end of the passage is always open, it is the friction with the sides of the passage that determines how much pressure resists the piston that packs wads of the straw or hay against the trailing end of the strand that is subdivided by the tying device into bales while still in the passage. Thus as the passage narrows, the friction increases as does the density of the bale and in fact it is the relative spacing of these side walls that is a principal factor, along with the consistency of the material being baled, in the density of the bales being produced.

German 38 20 367 describes a large-format square baler that picks the crop off the ground and packs it in a press passage in which a piston is reciprocated by a crank drive driven from a tractor power takeoff. The drive is supported at its upper side on a beam that is fixed on the side walls of the pressing passage. The rear end of the pressing passage is as described above formed by pivotal wall panels whose spacing can be changed hydraulically. The front wall of the pressing passage carries an inductive position sensor spaced closely to the beam so that its output indicates the amount of bend in this beam which is generally proportional to the force being exerted by the piston. This output is amplified and fed to a threshold discriminator. The output of the amplifier is smoothed and fed to an adding circuit and there compared to a set point. The position of the side-wall panels is adjusted in accordance with the difference.

Such an arrangement makes it possible to maintain the pressing force generally constant but does not really provide a readout of the actual density of the bales being produced. This density is affected by many factors, including the piston force, the composition of the material being baled, the moisture content of the material being baled, and the friction of the walls of the press passage.

European 0,223,350 and 0,223,351 describe an improvement on the system of DE 38 20 367. Here the crank drive for the pressing piston has a pair of piston rods that are each mounted at on end on the crank on the output shaft of the main drive and at the other end on bolts on the pressing piston. These bolts are provided with shear-force sensors in an annular array or with bend-type strain gauges. Thus the pressing force is measured directly, but as mentioned above this is only a factor in the bale's density and does not provide the equipment operator with an exact readout of bale density.

Finally, German 27 34 766 describes another large-format square baler wherein a pivotal side wall of the pressing passage is associated with a sensor and is urged into the passage so that its deflection is a measure of the compaction in the passage. This system is used with a set-point system as above to establish a standard compaction, but still does not give the operator of the machine a display or readout of the densities of the bales being produced.

OBJECTS OF THE INVENTION

It is therefore an object of the present invention to provide an improved baling system.

Another object is the provision of such an improved baling system which overcomes the above-given disadvantages, that is which automatically determines the exact density of each bale as it is produced, and that allows this density to be stored, displayed, and/or used to control the system.

SUMMARY OF THE INVENTION

Bales are produced by a baler having a pressing passage of predetermined cross section and from which emerges a succession of the bales that travel rearward from the press passage over an output guide and fall off a rear edge of the guide from the baler. The density of these bales is determined according to the invention by weighing each of the bales in the guide and producing a weight output corresponding to a weight of the bale in the guide and measuring the length of each of the bales in the guide and producing a length output corresponding to a length of the bale in the guide. Then the volume of each of the bales is calculated by multiplying the respective bale length output by an area equal to the cross section of the passage and each calculated volume is divided by the respective weight output to derive the density of the respective bale.

It is a relatively simple matter to continuously determine the bale densities in this manner by standard computer means. The length output Lx is multiplied by the cross-sectional area of the passage to produce a volume Vx which is then divided by the weight Gx for the bale, producing a density $\zeta$x for the bale in question. The density will be very exact and will allow the machine operator, if necessary, to adjust the baler to produce bales of different length and/or density while the machine is working. For instance if it is determined that the bales are too dense, the operator can decrease bale length by decreasing the cycle time of the tying device or can reduce back pressure on the bales by increasing the width of the pressing passage. Furthermore the computer can be connected to a level detector which compensates for any nonvertical position of the baler.

According to the invention the derived densities are averaged and displayed for a plurality of bales. Alternately the derived densities are averaged only over a predetermined limited time period.

The bale weight outputs are produced according to the invention by continuously monitoring the downward force with which the bales bear on the guide rear edge, continuously calculating an average of the monitored force, and establishing as a bale weight output the calculated average each time the calculated average peaks before the respective bale drops from the guide rear edge. The bale length outputs are produced by rotating a movable sensor element on the guide displaceable by the bales passing therealong and converting movement of the sensor element into an output corresponding to the respective length output of a bale passing thereover.

Both of these measurements can be made at the rear edge of the guide. Thus as the bale reaches a point where its center of mass is above or slightly rearward of the rear guide edge, the bale will tip up and its full weight will bear on the rear guide portion, so that the average weight will peak. From this position the bale will very quickly run off the rear edge, so that the downward force effective on the rear edge will rapidly decrease. Meanwhile, however the full length of the bale will slide or roll over this rear edge so this length can also be very accurately determined.

The downward force of the bale on the rear guide edge can be continuously monitored only in a time period immediately before and after a bale drops from the guide rear edge. This period can be synchronized to operation of the tying device which operates once each time a bale is completed in the press passage.

The derived bale densities and the lengths of the bales can be continuously displayed, along with total weights and/or lengths, for the operator of the machine who is normally on a tractor pulling the baler, although he or she could be in cabin of an automotive baler.

The apparatus for carrying out the method of this invention has sensor means for continuously monitoring the downward force with which the bales bear on the guide rear edge and computer means for continuously calculating an average of the monitored force and for establishing as an individual bale weight output the calculated average each time it peaks before a bale drops from the guide rear edge. In addition a movable sensor element on the guide is displaceable by the bales passing there-along and further electric circuitry connected to the sensor element converts movement of the sensor element into an output corresponding to the length of a ball passing thereover. The computer calculates the volume of each of the bales by multiplying the respective bale length output by an area equal to the cross section of the passage and for dividing each calculated volume by the respective weight output to derive the density of the respective bale.

The guide in accordance with the invention has a front end fixed to the baler and is pivotal on the baler at this front end. The apparatus further has according to the invention means for urging the guide rear end upward with a generally constant force. The sensor means detects deflection of the guide at the front edge. The guide is formed as roller conveyor and is provided at the rear edge with a roller over which the bales pass. The length measuring element can be provided at the rear edge of the guide or forward of a rear edge of the guide. In either case it is far enough downstream of the pressing passage that the bales have expanded to their finished length before contacting the length-measuring sensor.

It is also within the scope of the invention to determine the weight of each bale at two separate times and to average the two weights to determine the probable actual weight.

The guide is provided with an array of support rollers on which the bales are supported as they pass along the guide and the element is a wheel concentric with one of the rollers. The element can also be a pair of coaxially spaced wheels concentric with one of the rollers, with the elements' outputs being compared and the larger taken in order to cancel out any errors. Normally the element is a star wheel and the means connected to the sensor element includes a sensor disk rotationally attached to the star wheel. The star wheel has a predetermined number of radially projecting teeth engageable in the bales and the sensor disk has an edge formed with a multiplicity of notches. The notches are substantially more numerous than the teeth. The means connected to the sensor element includes a detector fixed adjacent the disk and capable of sensing the notches.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
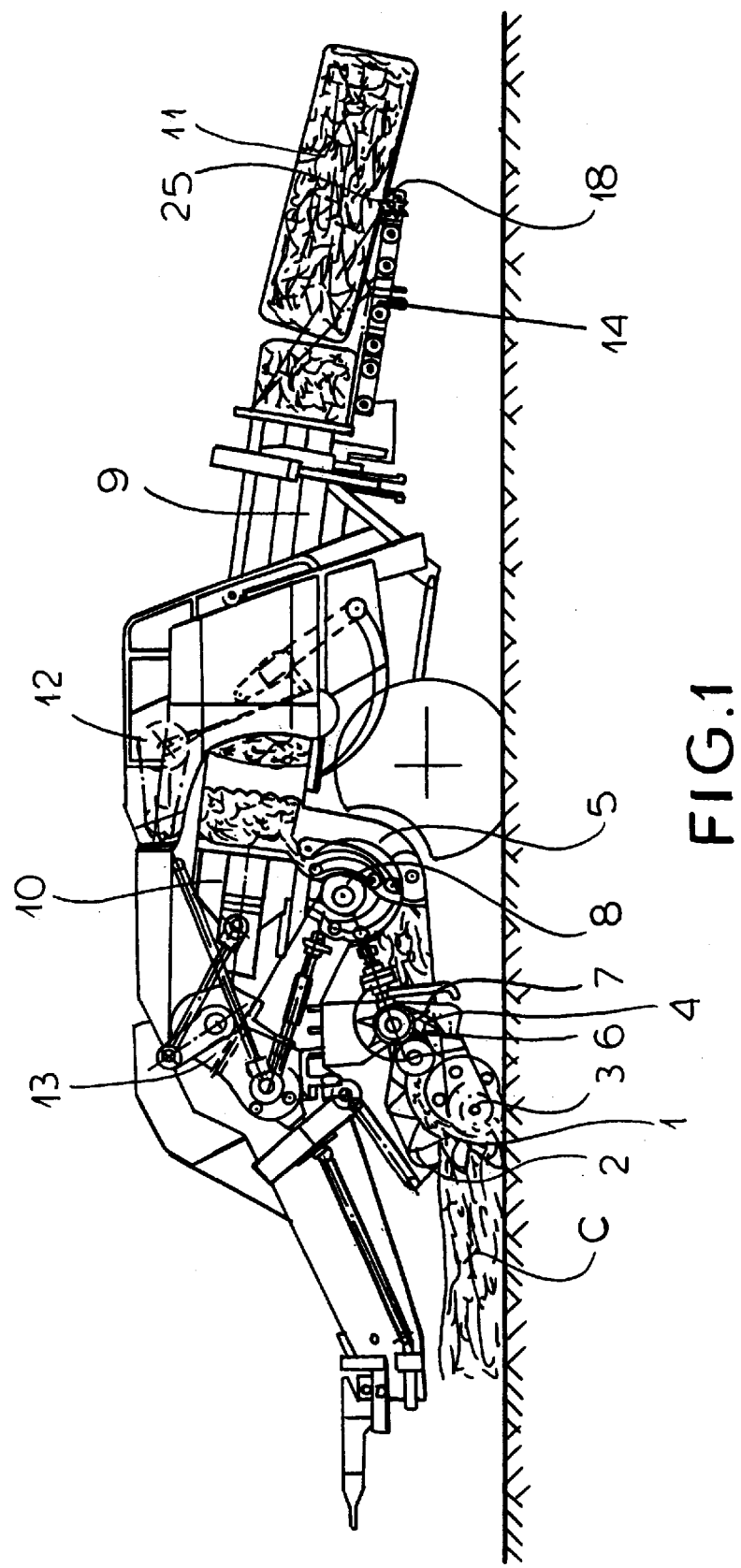
FIG. 1 is a small-scale partly diagrammatic and partly sectional side view of a baler according to the invention.

As seen in FIG. 1 a baler has on its front end a pickup 1 with teeth 2 that pick up windows of crop C from the ground on which the baler is supported by wheels 3. After the crop has been somewhat comminuted by a cutter 6 having cutting blades 7 an auger-type transverse conveyor 4 brings all the crop together into an input conduit 5. Another conveyor 8 presses the comminuted crop through the conduit 5 into a pressing passage 9 where a piston 10 forces it as bales 11 out a rear guide chute 15. A tying device 12 places standard wires or ties around the bales 11. Everything is powered from a drive 13 that is in turn connected to the power takeoff of the unillustrated tractor.

Figure 2:
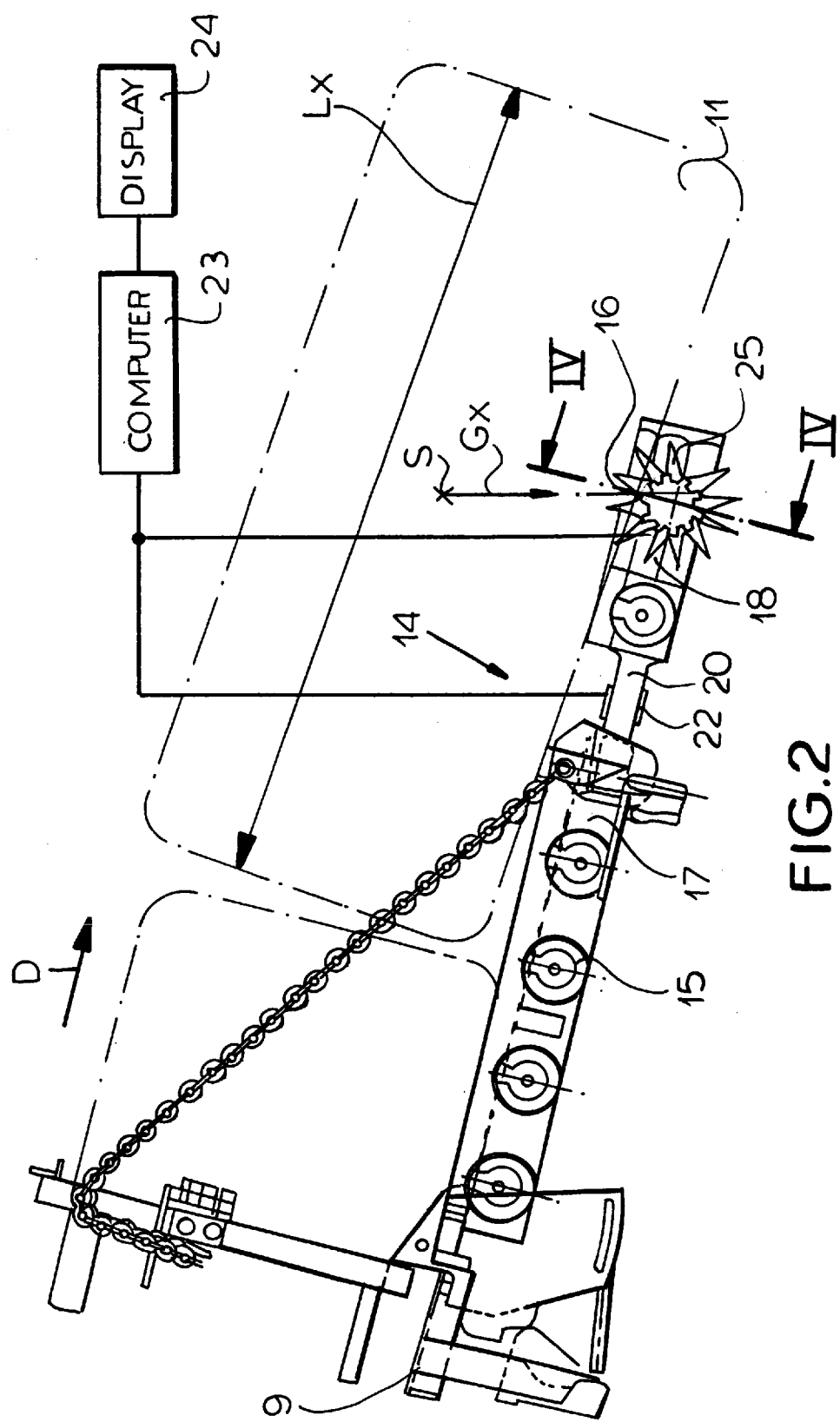
FIG. 2 is a larger-scale side view of the rear end of the baler.
Figure 3:
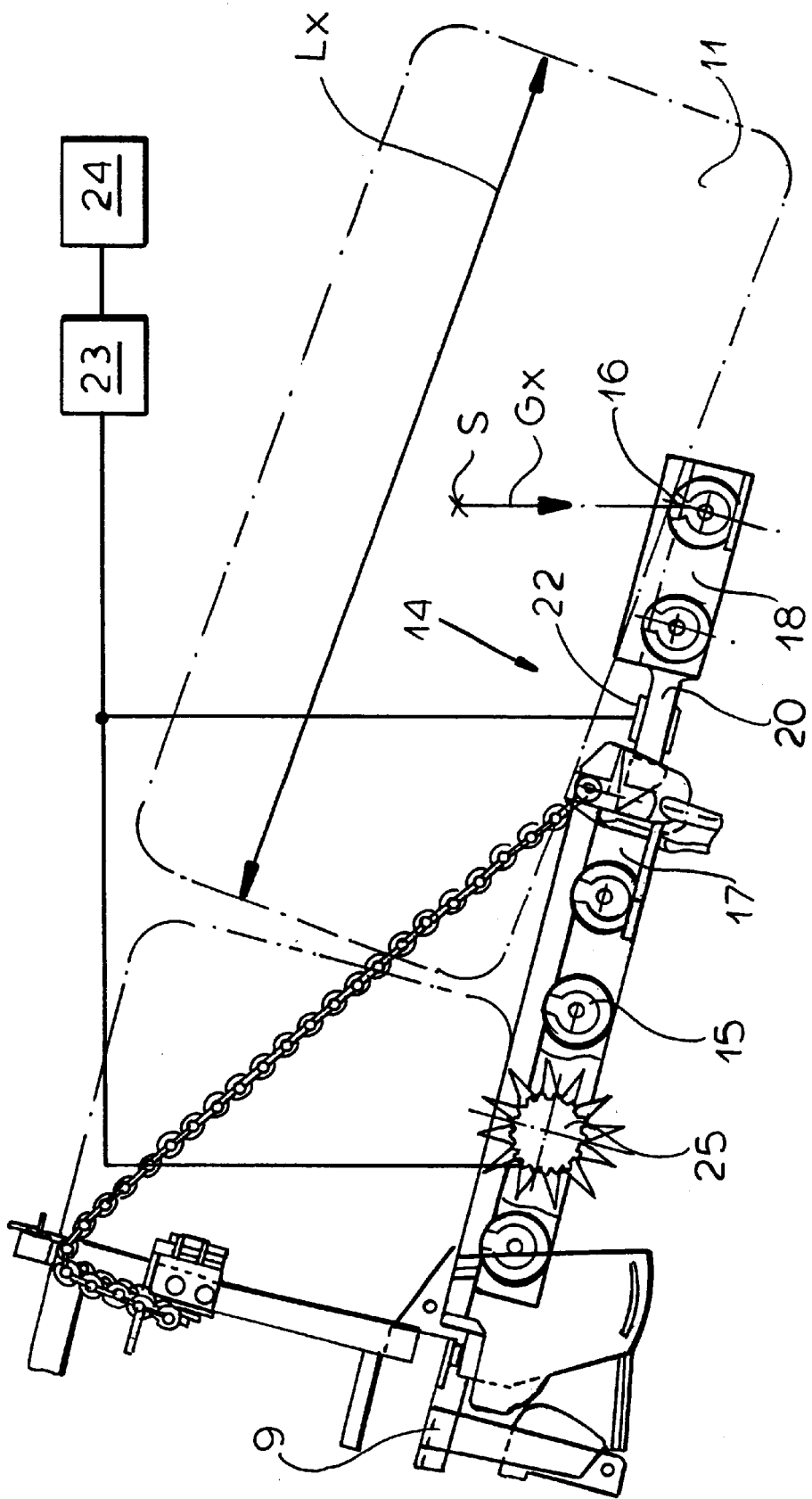
FIG. 3 is a lager-scale side view of the rear end of another baler according to the invention.
Figure 4:
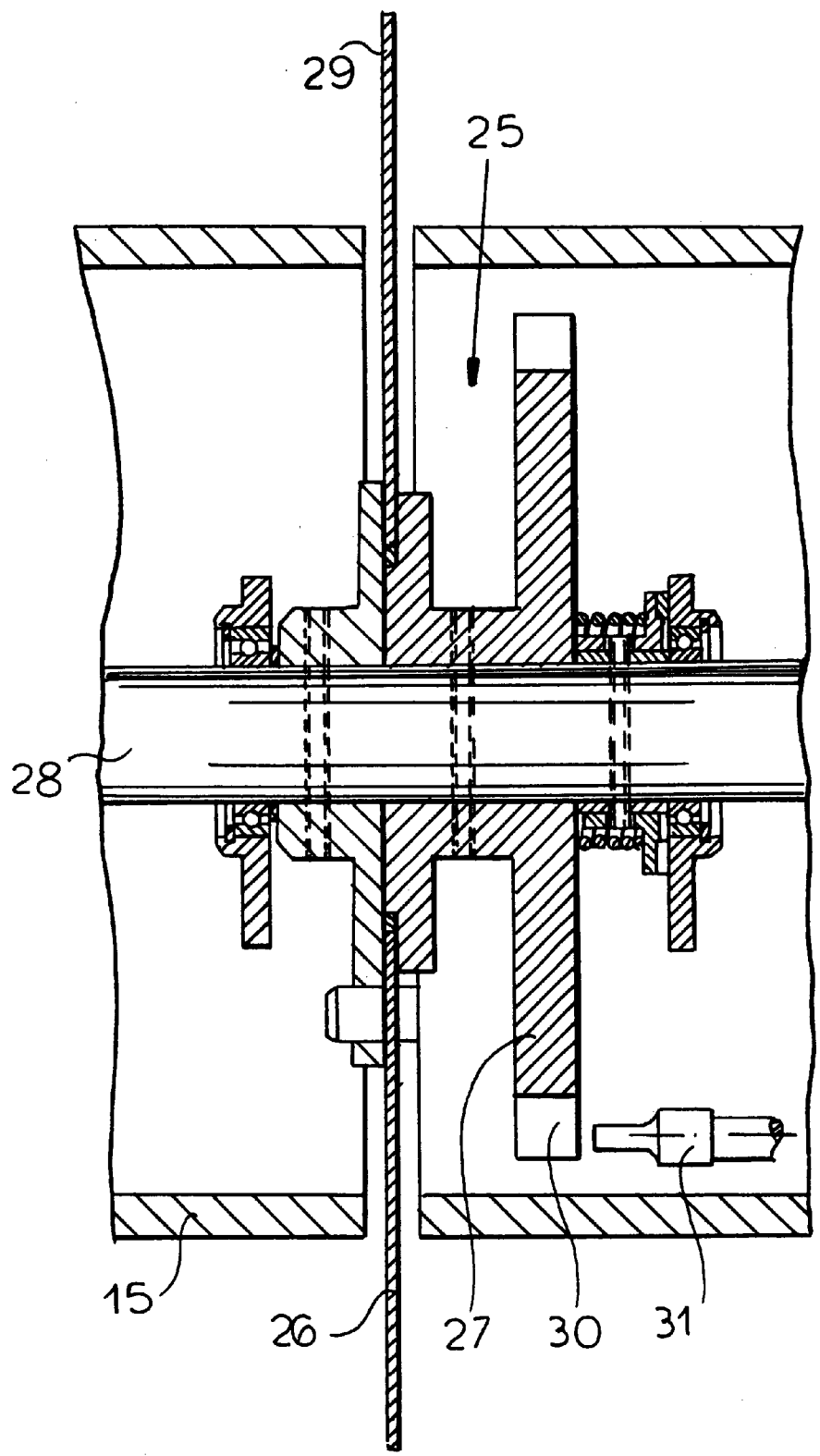
FIG. 4 is a section taken along line IV—IV of FIG. 2.
Figure 5:
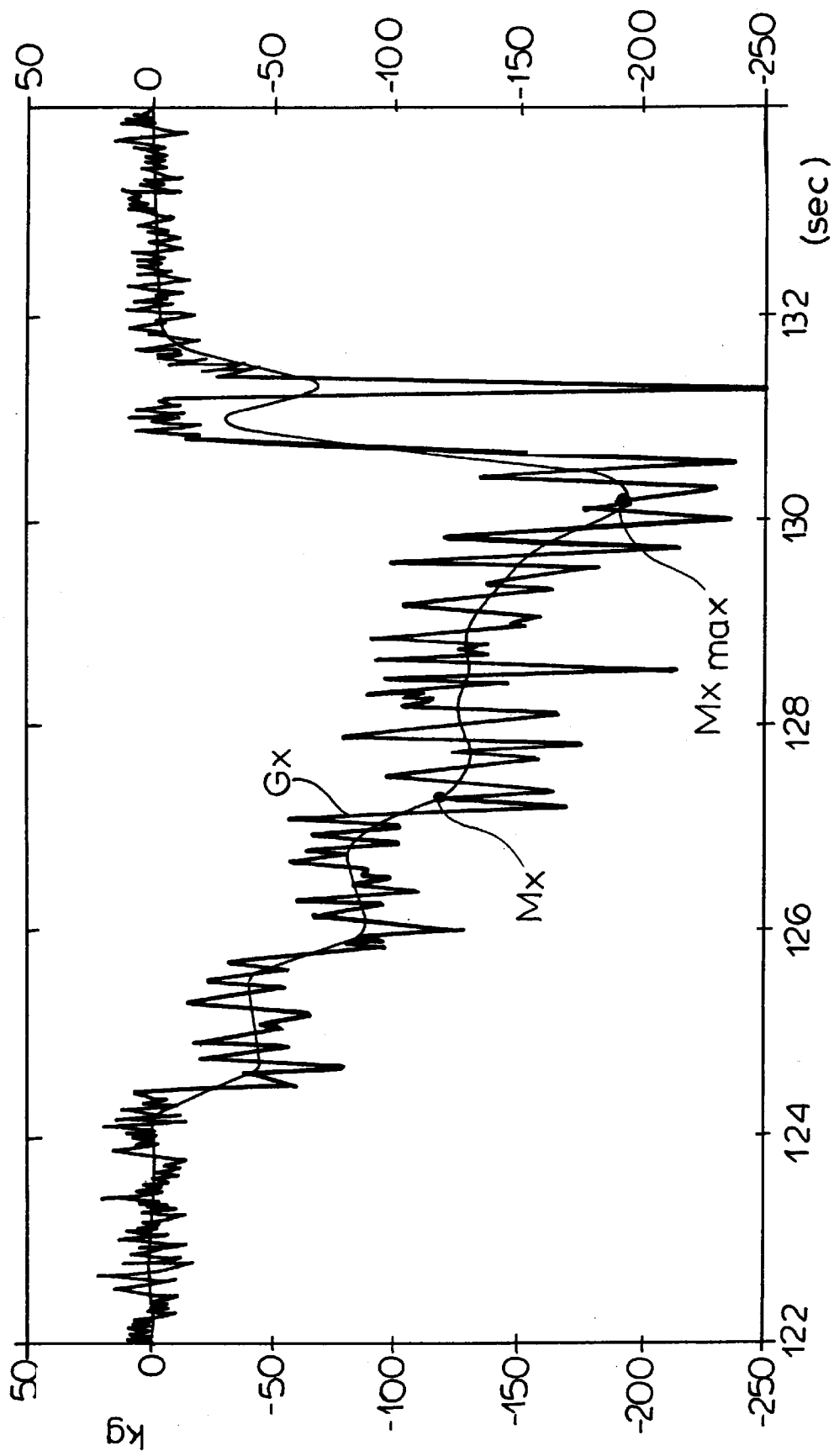
FIG. 5 is a graph illustrating how the invention functions.

The guide chute 14 at the rear end of the passage 9 has as shown in FIGS. 2 and 3 a support surface formed as a roller conveyor having a plurality of rollers 15 along which the bales 11 move in a transport direction D that is angled somewhat downward at the chute 14. The chute 14 is formed as described in more detail in copending application Ser. No. 09/368,102 by a front portion 17 that is essentially fixed to the rear end of the passage or tunnel 9, a flexible joint 20, and a rear end 18 forming a rear end or edge 16 at which is located one of the rollers 15.

According to the invention strain-gauge sensors 22 are provided on the upper and lower sides of the flexible pivot joint 20 so as to measure deflection of the portion 18 against the inherent resiliency of the joint 20 which tends to keep it parallel to the front portion 17.

The overall length of the rear portion 18 is less than half the length of the shortest bale 11 the machine is likely to produce. Thus as the bales 11 are pushed out, with the front end of one bale directly against the rear end of the preceding bale, the rearmost bale 11 will come to a position when its center of mass S will pass the rear end 16 and, for a few seconds, the full weight of each bale 11 is thus effective as a downward force Gx that will result in a predetermined downward deflection of the rear end 16. The sensors 22 can closely monitor the extent of this deflection, which is exactly proportional to the weight of the bale 11 being tipped off the back of the baler, and feed this information to a computer controller 23 on the baler frame.

FIG. 3 shows in accordance with this invention the downward force Gx exerted on the end 16 of the rear portion 18 plotted against time. As can be seen from second 122 to about second 125, when the rear portion 18 supports nothing, the mass detected varies by about 40 kg principally because the equipment is bouncing along rough ground. This variation is even more marked as the bale 11 starts to exert weight on the rear portion 18 until about second 131 when the bale drops off and the rear portion 18 snaps back up to await the next bale 11.

According to the invention the computer 25 calculates the average Mx of the instantaneously determined forces G1. This average Mx peaks or reaches a maximum $Mx_{max}$ just before the bale drops off. This maximum $Mx_{max}$ accurately represents the mass of the bale 11 being dropped. Here, some other factor, for instance the wheel of the baler dropping into a rut, has caused the value Gx to spike after the bale 11 was dropped, but since an average is being used this anomaly will not affect the reading.

A length sensor 25 is provided either at rear end 16 as shown in FIGS. 1 and 2 or somewhat forward thereof as shown in FIG. 3. This sensor 25 comprises one or more star wheels 26 coaxial with one of the rollers 15 and having a plurality of radially projecting teeth 29 that extend well above a plane defined by the rollers 15. The wheel 26 is fixed on a shaft 28 of the respective roller 15 and is coupled rotationally to a sensor disk 27 having an array of angularly equispaced and radially outwardly open edge notches 30 that can be detected by a stationary sensor 31 connected to the computer controller 23. The notches 30 are much more numerous than the teeth 29 so that the output of the sensor 31 will be a series of pulses each representing a predetermined angular displacement of the wheel 26. Two such sensor wheels 26 can be mounted for joint rotation about the same axis.

Thus as a bale 11 travels in the direction D over the sensor 25 it rotates the wheel 26 to an extent directly proportional to its length Lx. Since the bales 11 are out of the press passage 9 when their lengths Lx are measured, they have expanded to their full size so that an accurate measurement can be made. In particular the bale 11 as it runs over the rear edge 16, when the sensor 25 is mounted there, is completely decompressed and certain to ride with its entire length Lx on the wheel 26 which does not project horizontally from the guide 16 so that the rear end of the bale 11 will not rotate it as the bale 11 drops to the ground.

When the sensor 25 is mounted at the rear end 16, there will be a short period when it is not rotated at all. Thus the sensor 31 will produce a series of pulse trains each having a number of pulses directly proportional to the bale length Lx. When the sensor 25 is mounted somewhat forward of this location, the computer 23 is also connected to the tying device 12 so it can determine the cycling rate of the baler and break up the incoming stream of pulses into trains corresponding to the individual cycles. In both cases the individual bale lengths Lx are empirically measured and the measurements can be stored in the computer 23 so that a total bale length for a given field can be easily ascertained.

Since the width and height of the bales 11 are substantially fixed, the computer 23 can easily calculate the exact density of each bale. The known fixed width and height are multiplied by the bale length Lx to produce the bale's volume, which is divided by the bale's weight as determined by $Mx_{max}$. The result can be shown on a display 24 operated by the computer 23 and positioned right at the operator's station so that, if necessary, the operator can take action, for instance varying the width or height of the passage, to change the volume and, hence, the density. In addition of course the computer 23 can store the individual weights so as to determine the total weight of bales for a given field and so on.

I claim:

1. A method of determining the density of square bales produced by a baler having a pressing passage of predetermined cross section and from which emerges a succession of the bales that travel rearward from the press passage over an output guide and fall off the baler from a rear edge of the guide, the method comprising the steps of:

weighing each of the bales in the guide and producing a respective weight output corresponding to a weight of the bale in the guide;

measuring the length of each of the bales in the guide and producing a respective length output corresponding to a length of the bale in the guide;

calculating the volume of each of the bales by multiplying the respective bale length output by an area equal to the cross section of the passage; and dividing each calculated volume by the respective weight output to derive the density of the respective bale.

2. The density-determining method defined in claim 1, further comprising the step of averaging the derived densities and displaying the averaged derived density for a plurality of bales.

3. The density-determining method defined in claim 2 wherein the derived densities are averaged only over a predetermined limited time period.

4. The density-determining method defined in claim 1, wherein the bale weight outputs are produced by:

monitoring only the downward force with which the bales bear on the guide rear edge;

calculating an average of the monitored force;

establishing as a bale weight output the calculated average only as the calculated average peaks before the respective bale drops from the guide rear edge, the bale length outputs being produced by rotating a movable sensor element on the guide displaceable by the bales passing therealong; and converting movement of the sensor element into an output corresponding to the respective length output of a bale passing thereover.

5. The density-determining method defined in claim 1 wherein the weights of the bales are determined at the rear edge of the guide.

6. The density-determining method defined in claim 4 wherein the force is continuously monitored only in a time period immediately before and after a bale drops from the guide rear edge.

7. The density-determining method defined in claim 1, further comprising the step of displaying the derived bale densities.

8. The density-determining method defined in claim 1, further comprising the step of displaying the lengths of the bales.

\* \* \* \* \*